United States Patent
Rees et al.

(10) Patent No.: US 10,196,591 B2
(45) Date of Patent: Feb. 5, 2019

(54) GEL CLEANING COMPOSITION

(71) Applicant: S.C. Johnson & Son, Inc., Racine, WI (US)

(72) Inventors: Wayne M. Rees, Racine, WI (US); Thomas A. Strash, Kenosha, WI (US)

(73) Assignee: S. C. Johnson & Sons, Inc., Racine, WI (US)

( * ) Notice: Subject to any disclaimer, the term of this patent is extended or adjusted under 35 U.S.C. 154(b) by 94 days.

(21) Appl. No.: 15/195,514

(22) Filed: Jun. 28, 2016

(65) Prior Publication Data
US 2017/0009189 A1   Jan. 12, 2017

Related U.S. Application Data

(60) Provisional application No. 62/190,856, filed on Jul. 10, 2015, provisional application No. 62/348,382, filed on Jun. 10, 2016.

(51) Int. Cl.
| | |
|---|---|
| *C11D 1/72* | (2006.01) |
| *C11D 1/722* | (2006.01) |
| *C11D 3/18* | (2006.01) |
| *C11D 3/20* | (2006.01) |
| *C11D 3/37* | (2006.01) |
| *C11D 17/00* | (2006.01) |
| *C11D 11/00* | (2006.01) |
| *C11D 1/00* | (2006.01) |
| *C11D 1/825* | (2006.01) |

(52) U.S. Cl.
CPC ............ *C11D 17/003* (2013.01); *C11D 1/008* (2013.01); *C11D 1/72* (2013.01); *C11D 1/722* (2013.01); *C11D 1/825* (2013.01); *C11D 3/18* (2013.01); *C11D 3/2068* (2013.01); *C11D 3/2093* (2013.01); *C11D 3/3707* (2013.01); *C11D 11/0023* (2013.01); *C11D 17/0056* (2013.01)

(58) Field of Classification Search
CPC .. C11D 1/72; C11D 1/722; C11D 3/18; C11D 3/20; C11D 3/3707; C11D 17/003; C11D 17/0056
See application file for complete search history.

(56) References Cited

U.S. PATENT DOCUMENTS

| | | | |
|---|---|---|---|
| 3,578,499 A | 5/1971 | Crotty et al. | |
| 3,681,141 A | 8/1972 | Muoio | |
| 3,955,986 A | 5/1976 | Miller | |
| 4,578,207 A | 3/1986 | Holdt et al. | |
| 4,911,858 A | 3/1990 | Bunczk et al. | |
| 5,047,167 A | 9/1991 | Steyn et al. | |
| 5,254,290 A | 10/1993 | Blandizux et al. | |
| 5,336,427 A | 8/1994 | Bunczk et al. | |
| 5,460,742 A | 10/1995 | Cavanagh et al. | |
| 5,466,395 A | 11/1995 | Tosaka et al. | |
| 5,472,629 A | 12/1995 | Lysy et al. | |
| 5,562,850 A | 10/1996 | Woo et al. | |
| 5,579,842 A | 12/1996 | Riley | |
| 5,591,376 A | 1/1997 | Kiewert et al. | |
| 5,849,310 A | 12/1998 | Trinh et al. | |
| 5,877,135 A | 3/1999 | Hahn | |
| 5,985,808 A | 11/1999 | He et al. | |
| 6,087,309 A | 7/2000 | Vinson et al. | |
| 6,336,977 B1 | 1/2002 | Menke et al. | |
| 6,407,051 B1 | 6/2002 | Smith et al. | |
| 6,491,933 B2 | 12/2002 | Lorenzi et al. | |
| 6,667,286 B1 | 12/2003 | Dettinger et al. | |
| 6,914,075 B2 | 7/2005 | Nakano et al. | |
| 7,018,970 B1 | 3/2006 | Hsu et al. | |
| 7,727,948 B2 | 6/2010 | Mock-Knoblauch et al. | |
| 7,919,447 B1 | 4/2011 | Klinkhammer et al. | |
| 8,143,205 B2 | 3/2012 | Klinkhammer et al. | |
| 8,143,206 B2 | 3/2012 | Klinkhammer et al. | |
| 8,440,600 B2 | 5/2013 | Klinkhammer et al. | |
| 8,444,771 B2 | 5/2013 | Leipold et al. | |
| 8,461,093 B2 | 6/2013 | Leipold et al. | |
| 8,658,588 B2 | 2/2014 | Wortley et al. | |
| 8,835,371 B2 | 9/2014 | Leipold et al. | |
| 8,980,813 B2 | 3/2015 | Klinkhammer et al. | |
| 8,993,502 B2 | 3/2015 | Klinkhammer et al. | |
| 9,102,906 B2 | 8/2015 | Leipold et al. | |

(Continued)

FOREIGN PATENT DOCUMENTS

| | | |
|---|---|---|
| AU | 81384-91 | 11/1991 |
| EP | 0 631 788 | 1/1995 |
| EP | 1978080 A1 | 10/2008 |
| GB | 2 280 906 | 2/1995 |
| GB | 2 288 186 | 10/1995 |

(Continued)

OTHER PUBLICATIONS

PCT/US2016/040494 (Form PCT/ISA/206) Invitation to Pay Additional Fees and, Where Applicable, Protest Fee with Annex to Form PCT/ISA26 Communication Relating to the Results of the Partial International Search, dated Sep. 29, 2016.
PCT/US2016/040494 International Search Report and Written Opinion dated Nov. 23, 2016.
Abstract of JP A-6-141797 (1985).

*Primary Examiner* — Brian P Mruk

(57) ABSTRACT

Cleaning compositions in the form of a self-adhesive aqueous gel are provided. The aqueous gel may be a rigid, "hard" aqueous gel that resists deformation of its shape. The gel composition may desirably have a hardness of at least about 150 g and/or a gel melt temperature of about 50-90° C. The cleaning compositions may include a polyalkoxy nonionic surfactant, such as an alkoxylated alcohol and/or polymeric alkylene oxide block copolymer, a co-hardening agent, and water. Methods for treating a hard surface, such as a toilet bowl, using the cleaning compositions are also provided.

31 Claims, No Drawings

(56) References Cited

U.S. PATENT DOCUMENTS

| | | |
|---|---|---|
| 9,187,720 B2 | 11/2015 | Leipold et al. |
| 2003/0083210 A1 | 5/2003 | Goldberg et al. |
| 2003/0125220 A1 | 7/2003 | Dykstra et al. |
| 2006/0111262 A1 | 5/2006 | Conzelmann et al. |
| 2006/0204526 A1 | 9/2006 | Lathrop et al. |
| 2009/0215909 A1 | 8/2009 | Wortley et al. |
| 2009/0325839 A1 | 12/2009 | Wortley et al. |
| 2012/0108490 A1 | 5/2012 | Wortley et al. |
| 2012/0232170 A1 * | 9/2012 | Klinkhammer .......... C11D 3/18 514/789 |
| 2014/0037569 A1 | 2/2014 | Leipold et al. |
| 2014/0298577 A1 | 10/2014 | Burt et al. |
| 2014/0356311 A1 | 12/2014 | Leipold et al. |

FOREIGN PATENT DOCUMENTS

| | | | |
|---|---|---|---|
| WO | WO-97/05232 | 2/1997 | |
| WO | WO-97/40133 | 10/1997 | |
| WO | WO-02/26925 | 4/2002 | |
| WO | WO-03/066797 | 8/2003 | |
| WO | WO 2014/013234 * | 1/2014 | ............... A61L 9/05 |
| WO | WO 2014/013234 A1 | 1/2014 | |
| WO | WO 2015/091678 A1 | 6/2015 | |

\* cited by examiner

GEL CLEANING COMPOSITION

CROSS-REFERENCE TO RELATED APPLICATIONS

This patent application claims the benefit of U.S. Provisional Patent Application 62/190,856, filed on Jul. 10, 2015; and U.S. Provisional Patent Application 62/348,382, filed on Jun. 10, 2016; the entire contents of which are hereby incorporated by reference, for any and all purposes.

BACKGROUND

Cleaning compositions in gel form have utility for many household, industrial, and institutional applications. In most instances, such gels have "soft" and readily flowable rheological properties. In these instances, the cleaning products are generally dispensed from containers or devices and do not involve direct handling/physical manipulation of the cleaner formulation by the user. For some cleaning applications, however, handling/manipulation of the cleaner formulation may be highly desirable. The placement/adhesion of a unit dose of gel cleaner onto a toilet bowl, urinal, or shower wall surface, where the gel is intended to reside for an extended period of time, being slowly eroded/dissolved over time via repeated flushing with water, may be desirable. Self-adhering aqueous cleaning gel compositions are known for use as continuous hard surface cleaning systems, such as for flush toilets, wherein water passes over the gel with each flush of the toilet, thereby eroding or dissolving a minor amount of the composition with each flush and distributing cleaning ingredients to the toilet water and toilet bowl surface above and/or below the water line depending on the components of the gel. Other examples include placing a unit dose of gel cleaner into a designated dispensing chamber, such as a toilet bowl rimblock holder or the cleaner-dispensing cavity of an automatic dishwasher.

In cleaning applications such as these, it may be desirable to employ a rigid, "hard" aqueous gel that resists deformation of intended shape and that can be easily manufactured and subsequently handled by the end-user. It may also be desirable that unit doses of these gels retain their shape after manufacturing, up to and including when said gel products are handled by the end-user. To meet this requirement, such gels should desirably be resistant to heat-induced shape changes as packaged and stored after manufacturing, up to the end-use occasion. This includes storage of such products at reasonably anticipated elevated temperatures, such as a hot warehouse, shipping container, or end-use location. Since water is a major component of the gels, it is desirable that the gels are capable of being processed/manufactured at ambient atmospheric pressure and temperatures well below the boiling point of water.

SUMMARY

The present application relates generally to the field of cleaning compositions and, in particular, cleaning compositions which may be especially useful for cleaning hard surfaces, such as the inside surface of a toilet bowl. Aqueous gel cleaning compositions are described herein. Various embodiments of the gels may provide desirable manufacturing and handling properties for pre-measured unit doses, in particular highly desirable handling by the end-user. Such gels, having water as a major component, are low cost in nature and provide a favorable toxicity profile. Manufactured unit doses of the gels, due to compositional control of their "gel melt" temperature, may also commonly be resistant to deformation in shape even at elevated temperature. The processing of these aqueous gels can typically be accomplished at ambient atmospheric pressure and at temperatures well below the boiling point of water. The cleaning gels can be useful for the cleaning of hard surfaces, including for example, toilet bowls, urinals, shower enclosure and bath tub surfaces, dishes and other eating utensils, and the like.

Various embodiments of the present compositions provide aqueous gels which typically have self-adhesive properties, e.g., where the gel is self-adhering upon application to a hard surface. In some instances, the gel may adhere more strongly to the surface if it has already been wet with water. The aqueous gels commonly include nonionic surfactant, which includes a polyalkoxy group (also referred to herein as a "polyalkoxy nonionic surfactant"), a co-hardening agent and water, e.g., a gel including about 15 to 40 wt. % polyalkoxy nonionic surfactant, about 1 to 10 wt. % co-hardening agent, which may include a nonpolar hydrocarbon and/or an alkyl ester of an aliphatic acid, and at least about 25 wt. %, more commonly at least about 40 wt. % water. Typically, the polyalkoxy nonionic surfactant includes an average of at least about 15 alkylene oxide units, e.g., an average of at least about 15 ethyleneoxide and/or propyleneoxide units. The polyalkoxy nonionic surfactant may include an ethoxylated linear aliphatic alcohol and/or polymeric alkylene oxide block copolymer. The polyalkoxy nonionic surfactants employed in the present cleaning gels typically have an average molecular weight of at least about 600. Suitable EO—PO—EO block copolymers employed as a polyalkoxy nonionic surfactant commonly have an average molecular weight of at least about 1,000 and, often, about 1,000 to 5,000. Suitable alcohol—EO—PO block copolymers and/or alcohol—PO—EO block copolymers employed as a polyalkoxy nonionic surfactant commonly have an average molecular weight of at least about 600 and, often, about 600 to 2,000. Suitable ethoxylated aliphatic alcohols employed as a polyalkoxy nonionic surfactant commonly have an average molecular weight of at least about 1,000 and, often, about 1,000 to 2,000.

Various embodiments of the present compositions provide aqueous gels which typically have high hardness and rigidity. The composition commonly is a gel which may desirably have a hardness of at least about 150 g and/or a gel melt temperature of about 50-90° C. The cleaning compositions may include an alkoxylated alcohol (e.g., ethoxylated alcohol), polymeric alkylene oxide block copolymer (e.g., a ethylene oxide-propylene oxide block copolymer), a co-hardening agent, such as mineral oil, and water. In some embodiments, the cleaning compositions may include one or more additional components, such as a natural or synthetic polymer resin, a polyol humectant (such as glycerin, sorbitol, and/or other sugar alcohol), or an anionic surfactant and/or amphoteric surfactant and/or cationic surfactant and/or nonionic surfactant which is not an alkoxylated alcohol. Optionally, the cleaning compositions may also include one or more adjuvants, such as a fragrance, a complexing agent, and/or a bleaching agent. The ethoxylated alcohol component may include a mixture of ethoxylated alcohols having varying degrees of ethoxylation. For example, the ethoxylated alcohol component may include an ethoxylated $C_{14}$-$C_{30}$ alcohol having an average of about 20 to 50 ethylene oxide units and an ethoxylated $C_8$-$C_{18}$ alcohol having an average of about 5 to 15 ethylene oxide units. In some instances, the gel may be self-adhering upon application to a hard surface, typically a vertical or inclined hard surface.

The cleaning gel compositions contain water as a major component, and commonly include an ethoxylated $C_{16}$-$C_{30}$ alcohol, an ethylene oxide-propylene oxide block copolymer (which may act as a hardening agent), and a hydrocarbon or oxygenated hydrocarbon co-hardening agent. In some embodiments, the compositions may also include one or more secondary surfactant(s) distinct from both the $C_{16}$-$C_{30}$ ethoxylated alcohol and the ethylene oxide-propylene oxide block copolymer. Such compositions may also include a natural gum and/or synthetic polymer resin. Optional adjuvant ingredients also include fragrance, colorant(s), polyol humectant(s), preservative(s), antimicrobial agent(s), solvent(s), bleaching agent(s), abrasive(s), anti-scale agent(s), and/or pH adjusting agent(s), so long as such do not detrimentally alter the hardness and gel temperature of the present gels.

In some embodiments, the present technology may be a gel cleaning composition that includes an ethoxylated alcohol, a polymeric alkylene oxide block copolymer, co-hardening agent, such as mineral oil, and water. The cleaning compositions may optionally include a polyol humectant, such as glycerin, sorbitol and/or other sugar alcohol. In some embodiments, the composition is a gel having a hardness of at least about 150 g, more commonly at least about 200 g and/or a gel melt temperature of about 50-80° C. Often the cleaning compositions may include a fragrance component.

In another aspect, the cleaning composition may be a gel that includes a ethoxylated alcohol, which may be an ethoxylated $C_{16}$-$C_{30}$ alcohol having an average of 20 to 50 ethylene oxide units; the ethylene oxide-propylene oxide block copolymer, e.g., a EO—PO—EO block copolymer and/or a $C_{10}$-$C_{18}$ alcohol—EO—PO block copolymer; a co-hardening agent, such as mineral oil; and water.

In another embodiment, the cleaning composition may be a cleaning composition that includes about 15 to 40 wt. % of a first ethoxylated alcohol, which is an ethoxylated $C_{16}$-$C_{22}$ alcohol having an average of 20 to 50 ethylene oxide units; about 1 to 15 wt. % of the ethylene oxide-propylene oxide block copolymer; about 1 to 10 wt. % of the co-hardening agent; and water. In some aspects, the cleaning composition may also include a second ethoxylated alcohol, which is an ethoxylated $C_8$-$C_{18}$ alcohol having an average of about 5 to 15 ethylene oxide units. In some instances, the composition may be self-adhering upon application to a hard surface.

In some embodiments, the present compositions may provide consumers with the benefit of delivering a composition or active ingredient to a relatively wide area of a toilet bowl or other hard surface. In some embodiments, improved stability of a composition may be achieved through the inclusion in the composition of certain blends of ethoxylated alcohol(s) together with a polymeric alkylene oxide block copolymer, e.g., an ethylene oxide-propylene oxide block copolymer. In many embodiments, a dose of the composition on a hard surface (such as on or near the inside surface of a toilet bowl) can partially dissolve during and after each of periodic flows of water (e.g., toilet flushes) thereby providing a wet film, which typically emanates in all directions from the composition over the hard surface. The wet film which emanates from the dose over said hard surface can provide a delivery vehicle for components of the composition (e.g., cleaning agents such as detersive surfactants and/or scale dissolving agents) for immediate and residual treatment of the hard surface. The composition may be used to deliver in the wet film at least one active agent present in the composition to extended areas of the hard surface away from the predetermined position of the dose placement.

In certain aspects the present cleaning gels may be applied by hand directly on the hard surface to be treated, e.g. cleaned, such as a toilet bowl, urinal, shower or bath enclosure, drain, window, or the like, and may self-adhere thereto, including through a plurality of flows of water passing over the cleaning gel and surface, e.g. flushes, showers, rinses or the like. Each time water flows over the composition, a portion of the composition is released into the water that flows over the composition. The portion of the composition released into the water can provide a continuous wet film to the surface to, in turn, provide for immediate and long term cleaning and/or disinfecting and/or fragrancing or other surface treatment depending on the active agent(s) present in the composition. It is thought that the composition, and thus the active agents of the composition, may spread out from or are delivered from the initial composition placement in direct contact with the surface to coat continuously an extended area on the surface. The wet film may act as a coating and emanate from the self-adhering composition in all directions, i.e., 360 degrees, from the composition, which includes in a direction against the flow of the rinse water. Motions of the surface of a liquid are coupled with those of the subsurface fluid or fluids, so that movements of the liquid normally produce stresses in the surface and vice versa. The composition may be especially useful in treating the surface of a toilet bowl since it can allow for delivery and retention of a desired active agent on a surface above the water line in the bowl as well as below the water line.

DETAILED DESCRIPTION

In one aspect, the present cleaning composition may include a polyalkoxy nonionic surfactant, a co-hardening agent and at least about 25 wt. % water. The polyalkoxy nonionic surfactant commonly includes an average of at least about 15 alkylene oxide units, e.g., an average of at least about 15 ethyleneoxide and/or propyleneoxide units. The co-hardening agent may include a hydrocarbon and/or oxygenated hydrocarbon co-hardening agent, such as mineral oil, naphthenic oil, paraffin oil, an alkyl ester of an aliphatic acid, a $C_{12}$-$C_{18}$ aliphatic alcohol, and/or a $C_{10}$-$C_{18}$ aliphatic alcohol ethoxylate with an average degree of ethoxylation of no more than about 2. For example, cleaning composition may include water, a polyalkoxy nonionic surfactant, which includes an ethoxylated $C_{14}$-$C_{30}$ linear aliphatic alcohol, and a co-hardening agent, which includes mineral oil and/or an alkyl ester of a $C_{10}$-$C_{22}$ aliphatic acid.

In one aspect, the present cleaning composition may include an alkoxylated alcohol, an ethylene oxide-propylene oxide block copolymer, a co-hardening agent, such as mineral oil, and water. The cleaning composition may be a gel with a hardness value of at least about 150 grams. In some embodiments, the alkoxylated alcohol may include an ethoxylated alcohol, such as an ethoxylated $C_{16}$-$C_{30}$ aliphatic alcohol and typically an ethoxylated $C_{16}$-$C_{22}$ fatty alcohol having an average of about 20 to 50 ethylene oxide units.

In another aspect, the present cleaning composition may be a gel cleaning composition that includes: (a) ethoxylated alcohol; (b) polymeric alkylene oxide block copolymer; (c) a co-hardening agent; and (d) water. Typically, the composition is a rigid aqueous gel having a hardness of at least about 150 g and more commonly at least about 200 g. In some embodiments, the composition may self-adhere upon application to a hard surface.

In some embodiments, the composition may be a gel with a hardness of at least about 150 g. In some embodiments, the gel hardness may be at least about 200 g or more commonly at least about 250 g (as determined at 22° C.). The gel may have a gel melt temperature of about 50-90° C. In some embodiments, the gel melt temperature may be about 55-75° C. or often about 60-70° C. In some embodiments, the composition may be a gel with a hardness of at least about 150 g and a gel melt temperature of about 50 to 90° C.

The present compositions typically include about 15 to about 40 wt. % of at least one ethoxylated alcohol selected from the group consisting of $C_{14}$-$C_{30}$ alcohol ethoxylates with an average degree of ethoxylation in the range of about 20 to 50 moles of ethylene oxide per mole of alcohol, generally represented by the formula A:

(A)

where R=$C_{14}$-$C_{30}$ aliphatic group and x on average is 20-50.

It been found that a class of commercially available ethoxylated alcohols referred to as "narrow range" or "peaked" alcohol ethoxylates (hereinafter referred to as "peaked alcohol ethoxylates") may be particularly suitable for use as a polyalkoxy nonionic surfactant in the present compositions. The "narrow range" or "peaked" alcohol ethoxylates are typically produced with certain ethoxylation catalysts which result in an unusually narrow ethylene oxide population distribution range in the formed ethoxylated alcohol mixture. Commercial examples of these peaked alcohol ethoxylates include the Novel® alcohol ethoxylates, produced by Sasol North America Inc. Peaked alcohol ethoxylates, such as peaked aliphatic alcohol ethoxylates, can be prepared using the catalysts and methods described in U.S. Pat. No. 4,239,917, U.S. Pat. No. 4,223,164 and U.S. Pat. No. 8,329,609, the disclosures of which are herein incorporated by reference. The use of such materials have been found to produce gels of greater gel hardness without unacceptably high gel points (gel melt temperatures). Without being held to theory, the greater hardness of gels made from such ethoxylated alcohols is postulated to arise from the more uniform steric size of the surfactant polyethoxy (poly ethylene oxide) head group, allowing for more efficient gel structure formation. In addition, peaked alcohol ethoxylates such as the Novel® alcohol ethoxylates typically contain substantially less low molecular weight polyethylene glycol (PEG) impurity, a material which has been found to reduce gel hardness in the inventive compositions. The narrow range of the degree of ethoxylation and low PEG impurity characteristics for these peaked alcohol ethoxylate materials is described in the Novel® High Mole Ethoxylates Technical Bulletin, dated May 1, 2012, incorporated herein for reference. Typically, the peaked alcohol ethoxylates have a polyethylene glycol content of no more than about 1.5 wt. %. As a result, in many embodiments the present cleaning gels have a polyethylene glycol content of no more than about 0.5 wt. %. Typically, the peaked alcohol ethoxylates contain no more than about 0.5 wt. % residual alcohol (i.e., residual of the alcohol ROH corresponding to the "R group" in the structure shown above).

In some embodiments, the composition may include about 20-30 wt. % of this ethoxylated alcohol and often about 22-26 wt. %. In some embodiments, the ethoxylated alcohol may include a $C_{16}$-$C_{22}$ aliphatic group or more commonly a $C_{16}$-$C_{18}$ aliphatic group. In some embodiments, the aliphatic group may be an alkyl or alkenyl group. In some embodiments, the alkyl or alkenyl group is mostly unbranched (i.e.—a majority of the primary surfactant ethoxylated alcohol is derived from a linear alkyl or alkenyl alcohol). In some embodiments, the ethoxylated alcohol may include an average of about 20-35 ethylene oxide units, e.g., an average of about 25 ethylene oxide units. In some embodiments, the ethoxylated alcohol may include an ethoxylated $C_{16}$-$C_{18}$ aliphatic alcohol having an average of about 25 ethylene oxide units. Non-limiting examples of suitable primary surfactant ethoxylated alcohols include:

Genapol® T-250: $C_{16}$-$C_{18}$ Cetyl/Stearyl/Oleyl alcohol ethoxylate, 25 mole avg. ethoxylation, commercially available from Clariant Gmbh (Sulzbach, Germany);

Lutensol® AT-25: $C_{16}$-$C_{18}$ Cetyl/Stearyl natural hydrogenated alcohol ethoxylate, 25 mole avg. ethoxylation, commercially available from BASF Corp (Ludwigshafen, Germany); and Novel® 1618CG-25: $C_{16}$-$C_{18}$ Cetyl/Stearyl synthetic alcohol ethoxylate, 25 mole avg. ethoxylation, available from Sasol North America (Houston, USA).

In some embodiments, the composition may further include one or more of: (e) polyol humectant; (f) a fragrance component; (g) a nonionic surfactant which is different from the first ethoxylated alcohol; (h) a natural or synthetic polymer resin; (i) anionic, cationic, zwitterionic and/or amphoteric surfactant; and (j) one or more adjuvants. In some embodiments, the composition may further include an nonionic surfactant, e.g., an ethoxylated $C_8$-$C_{15}$ aliphatic alcohol having an average of 5 to 12 ethylene oxide units, which is different from the first ethoxylated alcohol. The adjuvants may include one or more adjuvants typically added to cleaning compositions, such as antimicrobial agent(s), water-soluble dye(s), pigment(s), complexing agent(s), surface modifying polymer(s), preservative agent(s), enzyme(s), bleach(es), pH adjusting agent(s), antiscale forming agent(s), abrasive(s), dispersant(s), and solvent(s).

The present compositions typically include a nonionic compound(s) based on a polymeric alkylene oxide block copolymer. The composition may include about 1 to 15 wt. % of the polymeric alkylene oxide block copolymer. In some embodiments, the composition may include about 2 to 12 wt. %, or more commonly about 3 to about 10 wt. % of the polymeric alkylene oxide block copolymer.

The polyalkoxy nonionic surfactants employed in the present cleaning gels typically have an average molecular weight of at least about 600. In some embodiments, the polymeric alkylene oxide block copolymer may include an ethylene oxide-propylene oxide block copolymer. The ethylene oxide-propylene oxide block copolymer may include an EO—PO block copolymer, an EO—PO—EO block copolymer, a $C_8$-$C_{18}$ alcohol EO—PO adduct, a $C_8$-$C_{18}$ alcohol PO—EO adduct, and/or an EO—PO dialkyl ether. The total molecular weight of such ethylene oxide-propylene oxide block copolymers is typically in the range of about 400 to 10,000 and, in some instances, about 500 to 5,000. In many instances, the ethylene oxide-propylene oxide block copolymer may suitably have an average molecular weight of at least about 600 or at least about 1,000, and commonly about 1,000 to 5,000. Unless expressly defined in a different manner, as used herein the term average molecular weight refers to the number average molar mass (also referred to as number average molecular weight or "$M_n$"). Suitable EO—PO—EO block copolymers employed as a polyalkoxy nonionic surfactant commonly have an average molecular weight of at least about 1,000 and, often, about 1,000 to 5,000. Suitable alcohol—EO—PO block copolymers and/or alcohol—PO—EO block copolymers employed as a polyalkoxy nonionic surfactant commonly have an average molecular weight of at least about 600 and, often, about 600 to 2,000. Suitable ethoxylated aliphatic alcohols employed as a polyalkoxy nonionic surfactant commonly have an average molecular weight of at least about 1,000 and, often, about 1,000 to 2,000.

Polymeric alkylene oxide block copolymers include nonionic compounds in which the major portion of the molecule is made up of block polymeric $C_2$-$C_4$ alkylene oxides. Such nonionic compounds, while often built up from an alkylene oxide chain starting group, can also have as a starting nucleus almost any active hydrogen containing group including, without limitation, alcohols (primary and/or secondary), amides, phenols, and thiols. In many embodiments, the present gels may contain about 3 to about 15 wt. % of at least one ethylene oxide (EO)—propylene oxide (PO) block copolymer, e.g., a compound of formula (B) and/or (C), below:

  (B)

  (C)

Quite commonly, the range of the ethylene oxide (EO)—propylene oxide (PO) block copolymer in the present gels is about 2 to 10 wt. %, often about 4 to 8 wt. %.

In the EO—PO—EO block copolymer structure represented by (B), EO represents ethylene oxide, PO represents propylene oxide, y commonly equals at least 15, and (EO) x+z typically equals at least about 10% and more commonly at least about 20% of the total weight of said compounds (and either x or z may be zero). Often, the total molecular weight of the alkylene oxide block copolymer is commonly in the range of about 400 to 10,000, more typically about 1,000 to 5,000. Exemplary useful EO/PO block copolymers are those materials commercially available under the trade name "Pluronic®," and in particular the Pluronic® L series, the Pluronic® P series, and the Pluronic® R series, each of which are block copolymers of propylene oxide and ethylene oxide, and are presently available from BASF AG (Ludwigshafen, Germany) and/or from BASF Corp. (Mt. Olive Township, N.J.). Examples of suitable nonionic block copolymers include EO—PO—EO block copolymers, such as Genapol® PF40 (with circa 40 wt. % EO units, Clariant Gmbh Sulzbach, Germany) and Pluronic® L64 ($M_n$~2900).

In the $C_{10}$-$C_{18}$ alcohol—EO—PO block copolymer structures represented by (C), R' represents an aliphatic group (typically a linear and/or branched alkyl and/or alkenyl group), typically having about 10 to 18 carbon atoms, EO represents ethylene oxide, PO represents propylene oxide, m commonly equals at least 2 and n commonly equals at least 2. Preferably both m and n are 4 or greater. The total molecular weight of the alkylene oxide block copolymer in structure (C) may be in the range of about 400 to 5,000, often about 400 to 2,000. Examples of useful ethylene oxide (EO)—propylene oxide (PO) block copolymers hardening agent compounds represented by structure (C) are commonly referred to commercially as alkoxylated alcohols. Specific examples of suitable EO—PO block copolymers for use in the present compositions include the Genapol® EP 25 series of C12/15 oxo alcohol EO—PO adducts (such as Genapol® EP 2584, Clariant Gmbh Sulzbach, Germany) and the Genapol® EP 24 series of lauryl alcohol EO—PO adducts (such as Genapol® EP 2454, Clariant Gmbh Sulzbach, Germany).

One suitable class of such nonionic surfactants containing the characteristic alkylene oxide blocks are those which may be generally represented by formula (D):

  (D)

where R represents an aliphatic group (typically a linear and/or branched alkyl and/or alkenyl group), commonly having about 10 to 18 carbon atoms, EO represents ethylene oxide, PO represents propylene oxide, y commonly equals at least 15, and (EO)x+z typically equals at least about 10% and more commonly at least about 20% of the total weight of such compounds. In some embodiments one of x and z may be zero. Examples of useful nonionic surfactant compounds which include as a major portion of the molecule a block polymeric alkylene oxide are those materials presently commercially available under the trade name Genapol® EP from Clariant Gmbh (Sulzbach, Germany). Such nonionic surfactants may include a $C_{10}$-$C_{15}$ alkyl group, e.g., an alkoxylated lauryl alcohol or alkoxylated C12/15 oxo alcohol.

Another suitable example includes a polyoxyethylene-polyoxypropylene block copolymer sold as (Lutrol F 127). This block copolymer has the following structure:

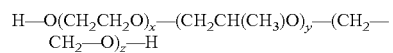

where x, z=~100, and y=~55

Another suitable polyoxyethylene-polyoxypropylene block copolymer is an EO—PO—EO block copolymer with 80% of polyethylene oxide in the molecule (sold by BASF as Pluronic PE 6800). Pluronic PE 6800 has a molecular weight of about 8,000 and includes a central polypropylene glycol group flanked by two polyethylene glycol groups. The polypropylene glycol block has a molecular weight of about 1750 (y~30) and a polyethylene glycol content (EO content) of about 80%.

The present gel compositions include co-hardening agent(s) having very low water solubility, typically soluble in water at less than about 0.1% by weight. The co-hardening agent may include a low vapor pressure, high flash point hydrocarbon or hydrocarbon mixture, such as mineral oil, naphthenic oil, or paraffin oil. Other suitable co-hardening agents include low vapor pressure, high flash point oxygenated hydrocarbons having very low water solubility, such as esters, fatty or synthetic alcohols, or $C_{10}$-$C_{18}$ alcohol ethoxylates with an average degree of ethoxylation of no more than about 2 and often about 1 mole of ethylene oxide per mole of alcohol. Examples of oxygenated hydrocarbons, suitable as co-hardening agents include alkyl esters of $C_{10}$-$C_{22}$ fatty acids, such as isopropyl myristate, $C_{12}$-$C_{16}$ aliphatic alcohols, and $C_{10}$-$C_{16}$ aliphatic alcohol ethoxylates with no more than about 2 mole average degree of ethoxylation, often with no more than about 1 mole average degree of ethoxylation, and typically mono-ethoxylates, such as the mono-ethoxylate of lauryl alcohol. The gel compositions may include about 1 to 10 wt. %, commonly about 1.5 to 5 wt. % of the co-hardening agent(s). In many instances, the gel composition includes about 1.5 to 3% of the co-hardening agent(s). The flash point of the co-hardening agent is generally about 90° C. or greater.

The present gel compositions may include a co-hardening agent, which includes an alkyl ester of an aliphatic carboxylic acid, such as an alkyl ester of a aliphatic carboxylic acid. Typically, the co-hardening agent includes a $C_1$-$C_6$ alkyl ester of a $C_{10}$-$C_{18}$ linear aliphatic carboxylic acid, e.g., a $C_2$-$C_6$ alkyl ester of a $C_{12}$-$C_{16}$ fatty acid. The aliphatic carboxylic acid alkyl ester commonly has a water solubility of no more than about 0.1 wt. % and/or a flash point of at least about 90° C. Suitable examples of the $C_{10}$-$C_{22}$ aliphatic acid alkyl ester include isopropyl myristate, ethyl palmitate, isopropyl palmitate, n-butyl myristate, n-hexyl laurate, ethyl stearate, isopropyl stearate, n-butyl laurate and ethyl oleate.

The co-hardening agent may also include mineral oil, naphthenic oil, paraffin oil, a $C_{12}$-$C_{18}$ aliphatic alcohol, and/or a $C_{10}$-$C_{18}$ aliphatic alcohol ethoxylate with an average degree of ethoxylation of no more than about 2 (and commonly an average degree of ethoxylation of no more than about 1).

The present compositions include water as a major component. The compositions may include at least about 25 wt. % water. More commonly, the compositions include at least about 40 wt. % water and, in some embodiments, at least about 50 wt. % water.

In some embodiments, the cleaning composition may optionally include one or more additional surfactants, such as anionic, cationic, zwitterionic, and/or amphoteric surfactant(s) and/or auxiliary nonionic surfactant(s), which is not an alkoxylated alcohol. Such cleaning compositions may optionally include one or more additional ingredients such as polyol humectants; natural gums and/or synthetic polymer resins; and/or adjuvants.

Many embodiments of the present gels may contain up to about 10 wt. % of at least one nonionic secondary surfactant selected from the group consisting of $C_8$-$C_{18}$ alcohol ethoxylates with an average degree of ethoxylation in the range of about 5-15 moles of ethylene oxide per mole of alcohol, distinct from the primary surfactant, the hardening agent, and the co-hardening agent. Commonly, the present gels contain about 2 to 6 wt. % of the nonionic alcohol ethoxylate secondary surfactant. The alcohol group of the non-ionic alcohol ethoxylate secondary surfactant may be linear or branched. Typically, when present, the ethoxylated alcohol secondary surfactant includes a $C_9$-$C_{15}$ linear and/or branched alcohol having an average of 5 to 15 ethylene oxide units. Non-limiting secondary surfactant examples are Genapol® X-100 (available from CLARIANT), which is a branched iso-$C_{13}$ alcohol ethoxylate having an average of 10 ethylene oxide units, Tomadol® 91-6—a $C_9$-$C_{11}$ ethoxylated alcohol having an average of 6 ethylene oxide units (available from Air Products and Chemicals, Inc.), LUTENSOL® AO-8—a synthetic $C_{13}$-$C_{15}$ ethoxylated oxo alcohol having an average of 8 ethylene oxide units (available from BASF), Genapol® LA 070S—an ethoxylated lauryl alcohol having an average of 7 ethylene oxide units (available from CLARIANT), and TERGITOL™ 15-S-7, a branched secondary ethoxylated alcohol with 7 ethylene oxide units (available from DOW Chemical).

Other exemplary useful nonionic surfactants include a variety of known nonionic surfactant compounds. Practically any hydrophobic compound having a carboxy, hydroxy, amido, or amino group with a free hydrogen attached to the nitrogen can be condensed with ethylene oxide or with the polyhydration product thereof, polyethylene glycol, to form a nonionic surfactant compound with varying degrees of water solubility—depending on the relative length of the hydrophobic and hydrophilic polyethylenoxy elements. Exemplary nonionic compounds include the polyoxyethylene ethers of alkyl aromatic hydroxy compounds, e.g., alkylated polyoxyethylene phenols, polyoxyethylene ethers of long chain aliphatic alcohols (e.g., ethoxylated alcohols), the polyoxyethylene ethers of hydrophobic propylene oxide polymers, and the higher alkyl amine oxides.

Further nonionic surfactants which may be optionally present in the aqueous cleaning compositions are alkyl polyglycosides. Suitable alkyl polyglycosides include known nonionic surfactants which are alkaline and electrolyte stable. Alkyl mono and polyglycosides are generally prepared by reacting a monosaccharide, or a compound hydrolyzable to a monosaccharide with an alcohol such as a fatty alcohol in an acid medium. The fatty alcohol may have from about 8 to 30 and typically 8 to 18 carbon atoms. Examples of such alkylglycosides include, APG 325 CS GLYCOSIDE which is reported to be a 50% $C_9$-$C_{11}$ alkyl polyglycoside (commercially available from Henkel Corp, Ambler, Pa.) and GLUCOPON® 625 CS which is reported to be a 50% $C_{10}$-$C_{16}$ alkyl polyglycoside.

Alkylpolyglycosides suitable for use in the present compositions may have the formula:

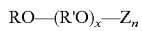

$$RO-(R'O)_x-Z_n$$

where R is a monovalent aliphatic radical containing 8 to 20 carbon atoms (the aliphatic group may be straight or branched, saturated or unsaturated), R' is a divalent alkyl radical containing 2 to 4 carbon atoms, preferably ethylene or propylene, x is a number having an average value of 0 to about 12, Z is a reducing saccharide moiety containing 5 or 6 carbon atoms, such as a glucose, galactose, glucosyl, or galactosyl residue, and n is a number having an average value of about 1 to 10. Some exemplary alkyl polyglycosides are sold under the name GLUCOPON® (where Z is a glucose moiety and x=0).

Additional suitable nonionic surfactants include linear alkyl amine oxides. Typical linear alkyl amine oxides include water-soluble amine oxides of the formula $R^1$—N$(R^2)(R^3)$O where $R^1$ is typically a $C_8$-$C_{18}$ alkyl moiety and the $R^2$ and $R^3$ moieties are typically selected from the group consisting of hydrogen, $C_1$-$C_3$ alkyl groups, and $C_1$-$C_3$ hydroxyalkyl groups. Quite often, $R^1$ is a $C_8$-$C_{18}$ n-alkyl and $R^2$ and $R^3$ are methyl, ethyl, propyl, isopropyl, 2-hydroxyethyl, 2-hydroxypropyl, and/or 3-hydroxypropyl. The linear amine oxide surfactants in particular may include linear $C_{10}$-$C_{18}$ alkyl dimethyl amine oxides and linear $C_8$-$C_{12}$ alkoxy ethyl di(hydroxyethyl) amine oxides. Particularly suitable amine oxides include linear $C_{10}$, linear $C_{10}$-$C_{12}$, and linear $C_{12}$-$C_{14}$ alkyl dimethyl amine oxides. Other examples of amine oxide nonionic surfactants include alkyl amidopropyl amine oxides, such as lauryl/myristyl amidopropyl amine oxides (e.g., lauryl/myristyl amidopropyl dimethylamine oxide).

Additional suitable nonionic surfactants include polyethoxylated fatty esters. These include, for example, polyethoxylated sorbitan monooleate, sorbitan monolaurate, sorbitan monopalmitate and/or sorbitan monostearate, and polyethoxylated castor oil. Specific examples of such surfactants are the products of condensation of ethylene oxide (e.g., 10-25 moles) with sorbitan monooleate and condensation of ethylene oxide (e.g., 20-40 moles) with castor oil.

In many embodiments, the present gels may contain up to about 10 wt. % polyol humectant(s). In some embodiments, the composition may include about 1-8 wt. % or more commonly about 2 to 6 wt. % of one or more polyol humectants. Examples of suitable polyol humectants include glycerin; glycols, such as ethylene glycol, propylene glycol, diethylene glycol, dipropylene glycol, butylene glycol and the like; sugar alcohols such as sorbitol, xylitol, and maltitol; sugars such as glucose, galactose, or compounds with glucosyl or galactosyl residues; and mixtures thereof.

In many embodiments, the present gels may contain up to about 1 wt. % polysaccharide(s) (such as a natural gum) and/or synthetic polymer resin(s). Nonlimiting suitable examples include polysaccharides and derivatives thereof, such as cellulose, sodium carboxymethyl cellulose, hydroxyethyl cellulose, hydroxypropyl cellulose, xanthan gum, agar, gellan gum, acacia gum, carob bean flour, guar gum, and starch.

In many embodiments, the present gels may contain up to about 10 wt. % of at least one auxiliary surfactant selected from the group consisting anionic, nonionic, cationic, zwitterionic and/or amphoteric surfactants, distinct from the $C_{16}$-$C_{30}$ alcohol ethoxylate, the EO—PO block copolymer hardening agent, and the $C_8$-$C_{18}$ alcohol ethoxylate nonionic secondary surfactant. Common classes of auxiliary surfactants include amine oxides, alkyl polyglucosides, alpha-olefin sulfonates, alkyl sulfates, alkylbenzene sulfonates, alkyl ether sulfates, and fatty acid alkanol amides.

The present cleaning compositions may include additional components or agents, such as additional functional materials (which may also be referred to as "adjuvants"). In some embodiments, the functional materials may be included to provide desired properties and functionalities to the cleaning composition. For the purpose of this application, the term "functional materials" include a material that when dispersed or dissolved in a concentrate and/or use solution, such as an aqueous solution, provides a beneficial property in a particular use. The present cleaning preparations containing the ionic liquids may optionally contain other soil-digesting components, surfactants, disinfectants, detergent fillers, sanitizers, acidulants, complexing agents, biocides, corrosion inhibitors, anti-redeposition agents, foam inhibitors, opacifying agents such as titanium dioxide, dyes, bleaching agents, enzymes, enzyme stabilizing systems, thickening or gelling agents, wetting agents, dispersants, stabilizing agents, dispersant polymers, cleaning compounds, and/or fragrances.

In many embodiments, the present gels may contain up to about 10 wt. % fragrance(s). Commonly, the present gels contain about 2 to 6 wt. % of fragrance(s).

The present cleaning compositions may contain up to about 10 wt. % of at least one cleaning adjuvant material selected from the group consisting of antimicrobial agent(s), water-soluble dye(s), pigment(s), complexing agent(s), stain preventers, surface modifying polymer(s), preservative agent(s), enzyme(s), bleaching agents (hydrogen peroxide and other peroxides), pH adjusting agent(s) (acids and alkaline agents), anti-scale forming agent(s), abrasive(s), dispersant(s), and solvent(s). Commonly employed cleaning adjuvant materials include dye(s), surface modifying polymer(s), preservative agent(s), and anti-scale forming agent(s).

In another embodiment, the composition may consist of (a) about 15-40 wt. % of an ethoxylated alcohol, which is an ethoxylated $C_{16}$-$C_{22}$ alcohol having an average of 20 to 50 ethylene oxide units; (b) about 1-10 wt. % of the ethylene oxide-propylene oxide block copolymer; (c) about 1.5-10 wt. % of a co-hardening agent, such as mineral oil; (d) at least about 40 wt. % water; (e) 0 to about 3 wt. % of a natural gum or synthetic polymer resin; (f) 0 to about 10 wt. % of a fragrance component; (g) 0 to about 15 wt. % of a polyol humectant; (h) 0 to about 10 wt. % of a nonionic surfactant which is different from the first ethoxylated alcohol; and (i) 0 to about 10 wt. % of one or more adjuvants.

As used herein, "gel" refers to a disordered solid composed of a liquid with a network of interacting particles or polymers which has a non-zero yield stress.

As used herein, "gel melt temperature" refers to the temperature at which the rigid gel composition abruptly transitions to a low viscosity flowable fluid having a viscosity of less than 5 Pa as the temperature of the gel is raised. To measure the gel melt temperature as defined herein, a Brookfield RS Plus Rheometer (Brookfield Engineering Laboratories, Inc., Middleboro, Mass.) was employed using a C25-1/30 cone/plate geometry with a 0.04 mm gap setting, a temperature ramp rate of 0.125° C./sec, and a constant shear rate of 1/sec. In one embodiment, the gel melt temperature may be at least about 50° C., at least about 55° C., or at least about 60° C. In another embodiment, the gel melt temperature may be no more than about 90° C., no more than about 80° C., or no more than about 70° C. The gel melt temperature may range from about 50° C. to 90° C. In some embodiments, the gel melt temperature may range from about 55° C. to 80° C. or more desirably from about 60° C. to 70° C.

As used herein, "gel hardness" is expressed in units of grams (g), and refers to the hardness/rigidity of a gel composition. The gel hardness values are determined by measurement at 22° C. using a Brookfield LFRA 1500 Texture Analyzer with TA41 probe (6 mm cylinder diameter, 35 mm length) with a trigger of 5.0 g, penetration distance of 3.0 mm, and a speed of 0.5 mm/sec, recorded as peak load values. In some embodiments, the present compositions may have a gel hardness of at least about 150 g. The compositions may have a gel hardness of at least about 175 g or at least about 185 g. The compositions may have a gel hardness of at least about 200 g. The compositions may have a gel hardness of at least about 225 g or at least about 250 g. In some embodiments, the gel hardness may range from about 150 g to 300 g. The gel hardness may range from about 175 g to 275 g or more commonly from about 185 g to 265 g. In some embodiments, the gel hardness may range from about 200 g to 250 g.

As used herein, "fragrance" refers to any perfume, odor-eliminator, odor masking agent, the like, and combinations thereof. In some embodiments, a fragrance is any substance which may have an effect on a consumer, or user's, olfactory senses.

As used herein, "wt. %" refers to the weight percentage of an ingredient in the total formula. For example, an off-the-shelf commercial composition of Formula X may only contain 70% active ingredient X. Thus, 10 g of the off-the-shelf composition only contains 7 g of X. If 10 g of the off-the-shelf composition is added to 90 g of other ingredients, the wt. % of X in the final formula is thus only 7%.

As used herein, "hard surface" refers to any porous and/or non-porous surface. In one embodiment, a hard surface may be selected from the group consisting of: ceramic, glass, metal, polymer, stone, and combinations thereof. For the purposes of this application, a hard surface does not include silicon wafers and/or other semiconductor substrate materials. Nonlimiting examples of ceramic surfaces include: toilet bowl, sink, shower, tile, the like, and combinations thereof. A non-limiting example of a glass surfaces includes: window and the like. Nonlimiting examples of metal surfaces include: drain pipe, sink, the like. Nonlimiting examples of a polymeric surface includes: PVC piping, fiberglass, acrylic, Corian®, the like. A non-limiting example of a stone hard surface includes: granite, marble, and the like.

A hard surface may be any shape, size, or have any orientation that is suitable for its desired purpose. In one non-limiting example, a hard surface may be oriented in a vertical configuration. In another non-limiting example, a hard surface may be the surface of a curved surface, such as a ceramic toilet bowl. In yet another non-limiting example, a hard surface may be the inside of a pipe, which has vertical and horizontal elements, and also may have curved elements. It is thought that the shape, size and/or orientation of the hard surface will not affect the present compositions, because of the unexpectedly strong transport properties of the compositions under the conditions described infra.

As used herein, "surfactant" refers to any agent that lowers the surface tension of a liquid, for example water. Exemplary surfactants which may be suitable for use with the present compositions are described infra. In one embodiment, surfactants may be selected from the group consisting of anionic, non-ionic, cationic, amphoteric, zwitterionic, and combinations thereof. In one embodiment, the cleaning composition may be substantially free of a cationic surfactant. In some embodiments, the cleaning composition may be substantially free of an anionic surfactant.

provide a hardness value of at least 150 g. These compositions include a $C_{16}$-$C_{18}$ alcohol ethoxylate primary surfactant (i.e., Genapol® T-250), ethylene oxide-propylene oxide block copolymer, mineral oil, and water. In comparison, compositions in Table 1 that did not include at least the 4 components had a hardness value less than 150 g. For example, samples A, B, and H-M did not include an ethylene oxide-propylene oxide block copolymer and had hardness values ranging from 73.5-130.2 g.

TABLE 1

| Gel Ingredient | A | B | C | D | E | F | G | H | I |
|---|---|---|---|---|---|---|---|---|---|
| Deionized Water (wt. %) | 58.00 | 56.00 | 58.00 | 56.00 | 56.00 | 56.00 | 56.00 | 56.00 | 56.00 |
| Genapol ® T-250 (wt. %) | 24.00 | 24.00 | 24.00 | 24.00 | 24.00 | 24.00 | 24.00 | 24.00 | 24.00 |
| EO-PO Block Co-Polymer Surfactant (wt. %) | 0.00 | 0.00 | 4.00 | 4.00 | 4.00 | 4.00 | 4.00 | 0.00 | 0.00 |
| Genapol ® X-100 (wt. %) | 8.00 | 8.00 | 4.00 | 4.00 | 4.00 | 4.00 | 4.00 | 4.00 | 4.00 |
| Secondary Nonionic Surfactant (wt. %) | 0.00 | 0.00 | 0.00 | 0.00 | 0.00 | 0.00 | 0.00 | 4.00 | 4.00 |
| Fragrance (wt. %) | 5.00 | 5.00 | 5.00 | 5.00 | 5.00 | 5.00 | 5.00 | 5.00 | 5.00 |
| Glycerin (wt. %) | 5.00 | 5.00 | 5.00 | 5.00 | 5.00 | 5.00 | 5.00 | 5.00 | 5.00 |
| Mineral Oil (wt. %) | 0.00 | 2.00 | 0.00 | 2.00 | 2.00 | 2.00 | 2.00 | 2.00 | 2.00 |
| Hardness Value (grams) | 73.5 | 106.5 | 85.9 | 221 | 220.9 | 235.8 | 201.9 | 99.7 | 95.3 |
| Gel Point (° C.) | 48 | 67 | 47 | 63 | 65 | 71 | 71 | 62 | 66 |

| Gel Ingredient | J | K | L | M | N | O | P | Q |
|---|---|---|---|---|---|---|---|---|
| Deionized Water (wt. %) | 56.00 | 56.00 | 56.75 | 56.00 | 56.75 | 55.50 | 61.00 | 56.0 |
| Genapol ® T-250 (wt. %) | 24.00 | 24.00 | 28.00 | 28.00 | 24.00 | 24.00 | 24.00 | 24.00 |
| EO-PO Block Co-Polymer Surfactant (wt. %) | 0.00 | 0.00 | 0.00 | 0.00 | 4.00 | 4.00 | 8.00 | 8.00 |
| Genapol ® X-100 (wt. %) | 4.00 | 4.00 | 4.00 | 4.00 | 4.00 | 4.00 | 0.00 | 0.00 |
| Secondary Nonionic Surfactant (wt. %) | 4.00 | 4.00 | 0.00 | 0.00 | 0.00 | 0.00 | 0.00 | 0.00 |
| Fragrance (wt. %) | 5.00 | 5.00 | 5.00 | 5.00 | 5.00 | 5.00 | 5.00 | 5.00 |
| Glycerin (wt. %) | 5.00 | 5.00 | 5.00 | 5.00 | 5.00 | 5.00 | 0.00 | 5.00 |
| Mineral Oil (wt. %) | 2.00 | 2.00 | 0.00 | 2.00 | 1.25 | 2.50 | 2.00 | 2.00 |
| Hardness Value (grams) | 99.5 | 97.7 | 86.3 | 130.2 | 95.8 | 241.9 | 239.6 | 238.9 |
| Gel Point (° C.) | 67 | 64 | 63 | 80 | 59 | 67 | 69.6 | 67.7 |

As used herein, "self-adhering" or "self-adhesive" refers to the ability of a composition to stick onto a hard surface without the need for a separate adhesive or other support device. In one embodiment, a self-adhering composition does not leave any residue or other substance (i.e., additional adhesive) once the composition is used up.

As used herein, "substantially free" refers to a composition that includes less than about 0.1 wt. %, or is absent of any detectable amount of the referenced component.

EXAMPLES

The following examples illustrate more specifically the present cleaning compositions according to various embodiments described above. These examples should in no way be construed as limiting the scope of the present technology.

Several exemplary formulations of the cleaning compositions were prepared and are presented in Tables 1-3. For each formulation, the hardness and gel melt temperatures were measured as described herein. As shown in Table 1, exemplary formulation samples D, E, F, G, O, P, and Q Where a "secondary nonionic surfactant," other than Genapol® X-100, was included in the formulations in Table 1, the secondary nonionic surfactant was selected from Tomadol® 91-6 (sample H), LUTENSOL® AO-8 (sample I), Genapol® LA 070S (sample J), and TERGITOL™ 15-S-7 (sample K). The EO—PO block co-polymer surfactant was selected from Genapol® EP 2584 (samples C, D, and N-Q), Genapol® EP 2454 (sample E), Genapol® PF40 (sample F), and Pluronic L64 (sample G).

A typical gel hardness value for a desirable gel composition may be about ≥150 g or higher (i.e., suitable for hand-held manipulation of the gel). The compositions indicate that as the amount of mineral oil increased the hardness of the sample increased. Comparing compositions C, D, N, and O indicates that the inclusion of a combination of an EO—PO block copolymer with mineral oil may be common for the composition to exhibit acceptable gel hardness. Compositions A, B, and H-M did not achieve a gel hardness of ≥150 g. These compositions did not include an EO—PO block co-polymer, but did contain various combinations of other nonionic surfactants and 2.0 wt. % mineral oil.

Accordingly, there will typically be a minimum amount of EO—PO block copolymer and co-hardening agent such as mineral oil in the compositions that provide desirable hardness levels, such as a level of mineral oil greater than about 1.25 wt. % and/or a level of EO—PO block copolymer of at least about 4 wt. %.

Compositions D-G and O-Q achieve a gel hardness of at least 150 g. These compositions included an EO—PO block copolymer and at least 2 wt. % mineral oil. Compositions D-G used differing EO—PO block copolymers (Genapol® EP 2584, Genapol® EP 2454, Genapol® PF40, or Pluronic L64). Compositions D-G and O also included Genapol® X-100. In comparison, composition Q did not include Genapol® X-100 or any secondary nonionic surfactant. The varying formulations indicate the gel hardness effect of at least 150 g can be achieved using various EO—PO block copolymers and that neither Genapol® X-100 nor any secondary nonionic surfactant are necessary to achieve the combination of a gel hardness of at least 150 g and a gel melt temperature ranging from about 50-90° C.

Additional exemplary formulations of the cleaning compositions were prepared and are presented in Table 2. Samples R, S, and T illustrate that various $C_{16}$-$C_{18}$ alcohol ethoxylates with approximately 25 ethylene oxide units and varying alcohol groups can provide compositions with a gel hardness of at least 150 g. Notably, composition T, formulated using a Novel® "peaked" alcohol ethoxylate exhibits a substantially higher gel hardness than closely related compositions R and S, which have substantially identical formulations except for the source of the $C_{16}$/$C_{18}$ alcohol ethoxylate with 25 mole avg. ethoxylation. Composition T has the highest gel hardness observed amongst the various illustrative examples described herein.

TABLE 2

| Gel Ingredient | R | S | T |
| --- | --- | --- | --- |
| Deionized Water (wt. %) | 61.12 | 61.15 | 61.15 |
| Genapol T-250 (wt. %) | 23.00 | 0.00 | 0.00 |
| Lutensol AT-25 (wt. %) | 0.00 | 23.00 | 0.00 |
| Novel 1618CG-25 (wt. %) | 0.00 | 0.00 | 23.00 |
| Genapol EP-2584 EO-PO Copolymer (wt. %) | 4.00 | 4.00 | 4.00 |
| Genapol LA-070 (wt. %) | 4.50 | 4.50 | 4.50 |
| Xanthan Gum (wt. %) | 0.03 | 0.03 | 0.03 |
| Mineral Oil (wt. %) | 2.35 | 2.35 | 2.35 |
| Fragrance (wt. %) | 5.00 | 5.00 | 5.00 |
| Hardness Value (grams) | 234.7 | 229.2 | 275.3 |
| Gel Point (° C.) | 61 | 55 | 59 |

Genapol ® T-250: $C_{16}$-$C_{18}$ Cetyl/Stearyl/Oleyl alcohol ethoxylate, 25 mole avg. ethoxylation, commercially available from Clariant Gmbh (Sulzbach, Germany);
Lutensol ® AT-25: $C_{16}$-$C_{18}$ Cetyl/Stearyl natural hydrogenated alcohol ethoxylate, 25 mole avg. ethoxylation, commercially available from BASF Corp (Ludwigshafen, Germany); and
Novel ® 1618CG-25: $C_{16}$-$C_{18}$ Cetyl/Stearyl synthetic alcohol ethoxylate, 25 mole avg. ethoxylation, available from Sasol North America (Houston, USA).

Table 3 includes four additional exemplary formulations of the cleaning compositions. Samples R, U, V, W, and X illustrate that various co-hardening agents with differing chemical structure/functional groups result in a gel hardness of ≥150 g (R is mineral oil; U is naphthenic oil; V is isopropyl myristate; W is Alfol 1216 Alcohol (synthetic $C_{12}$-$C_{16}$ alcohol blend, available from Sasol Corp.); X is Genapol LA 010 (lauryl alcohol ethoxylate, 1 mole average EO, available from Clariant Corp.)).

TABLE 3

| Gel Ingredient | R | U | V | W | X |
| --- | --- | --- | --- | --- | --- |
| Deionized Water (wt. %) | 61.12 | 61.20 | 61.20 | 61.20 | 61.20 |
| Genapol T-250 (wt. %) | 23.00 | 23.00 | 23.00 | 23.00 | 23.00 |
| Genapol EP-2584 EO-PO Copolymer (wt. %) | 4.00 | 4.00 | 4.00 | 4.00 | 4.00 |
| Genapol LA-070 (wt. %) | 4.50 | 4.50 | 4.50 | 4.50 | 4.50 |
| Co-Hardening Agent (wt. %) | 2.35 | 2.30 | 2.30 | 2.30 | 2.30 |
| Fragrance (wt. %) | 5.00 | 5.00 | 5.00 | 5.00 | 5.00 |
| Xanthan Gum (wt. %) | 0.03 | 0.00 | 0.00 | 0.00 | 0.00 |
| Hardness Value (grams) | 234.7 | 232.1 | 228.1 | 215.9 | 170.4 |
| Gel Point (° C.) | 61 | 58 | 60 | 57 | 54 |

ILLUSTRATIVE EMBODIMENTS

While certain embodiments have been illustrated and described, it should be understood that changes and modifications can be made therein in accordance with ordinary skill in the art without departing from the technology in its broader aspects.

In one aspect, the cleaning composition may include (a) ethoxylated alcohol; (b) polymeric alkylene oxide block copolymer; (c) a co-hardening agent, such as mineral oil; and (d) water. In some embodiments, the composition may have a hardness of at least about 150 g at 22° C. In some embodiments, the gel may have a gel melt temperature of about 50 to 90° C. In some embodiments, the ethoxylated alcohol may have an average of 20 to 50 ethoxy units. In some embodiments, the polymeric alkylene oxide block copolymer may include a ethylene oxide-propylene oxide block copolymer. The ethylene oxide-propylene oxide block copolymer may include an EO—PO block copolymer, an EO—PO—EO block copolymer, a $C_8$-$C_{18}$ alcohol EO—PO adduct, a $C_8$-$C_{18}$ alcohol PO-EO adduct, and/or an EO—PO dialkyl ether.

In some embodiments, the ethoxylated alcohol may include ethoxylated $C_{16}$-$C_{30}$ alcohol; and the polymeric alkylene oxide block copolymer may include an ethylene oxide-propylene oxide block copolymer. The composition may include: (a) about 15 to 40 wt. % of the ethoxylated alcohol, which may include an ethoxylated $C_{16}$-$C_{22}$ alcohol having an average of 20 to 50 ethylene oxide units; (b) about 3 to 15 wt. % of the ethylene oxide-propylene oxide block copolymer; (c) about 1.5 to 10 wt. % of the co-hardening agent; and (d) at least about 25 wt. % water. In some embodiments, the ethylene oxide-propylene oxide block copolymer may include an EO—PO—EO block copolymer and/or a $C_{10}$-$C_{18}$ alcohol-EO—PO block copolymer. The ethylene oxide-propylene oxide block copolymer may have molecular weight of about 400 to 5,000. In some embodiments, the ethylene oxide-propylene oxide block copolymer may include an EO—PO—EO block copolymer and/or a $C_8$-$C_{18}$ alcohol EO—PO adduct.

In some embodiments, the co-hardening agent may include mineral oil, naphthenic oil, paraffin oil, an alkyl ester of a $C_{10}$-$C_{22}$ fatty acid, a $C_{10}$-$C_{22}$ alcohol and/or a $C_{10}$-$C_{22}$ alcohol ethoxylate with no more than about 1 mole average degree of ethoxylation, or combinations thereof. The co-hardening agent may have a water solubility of no more than about 0.1 wt. %. The co-hardening agent may have a flash point of at least about 90° C.

In some embodiments, the composition may further include fragrance, colorant, polyol humectant, preservative, antimicrobial agent, solvent, bleaching agent, abrasive, anti-scale agent, and/or pH adjusting agent. In some embodiments, the composition may further include a polysaccharide and/or synthetic polymer resin.

In some embodiments, the ethylene oxide-propylene oxide block copolymer may include an EO—PO—EO block copolymer represented by Formula (B):

HO—(EO)$_x$(PO)$_y$(EO)$_z$—H                              (B)

wherein EO represents an ethylene oxide unit, PO represents a propylene oxide unit, y is an integer of at least 15, and (EO)x+z constitutes at least about 10% of the total weight of the EO—PO—EO block copolymer. In some embodiments, the ethylene oxide-propylene oxide block copolymer may include an $C_{10}$-$C_{18}$ alcohol-EO—PO block copolymer represented by Formula (C):

R'O—(EO)$_m$(PO)$_n$H                              (C)

wherein EO represents an ethylene oxide unit, PO represents a propylene oxide unit, n is an integer of at least 2, m is an integer of at least 2, and the $C_{10}$-$C_{18}$ alcohol-EO—PO block copolymer has a molecular weight of about 400 to 5,000.

In some embodiments, the composition may include: (a) about 20 to 35 wt. % of the ethoxylated alcohol, which may include an ethoxylated $C_{16}$-$C_{22}$ linear alcohol having an average of 20 to 30 ethylene oxide units; (b) about 3 to 10 wt. % ethylene oxide-propylene oxide block copolymer; (c) about 1.5 to 5 wt. % of the co-hardening agent; and (d) at least about 40 wt. % water. The composition may further include (e) about 1-10 wt. % of a fragrance component; and optionally include polyol humectant and/or natural gum thickener.

In some embodiments, (a) the ethoxylated alcohol may include an ethoxylated $C_{16}$-$C_{22}$ linear aliphatic alcohol which may have an average of 20 to 30 ethylene oxide units; (b) the polymeric alkylene oxide block copolymer may have a molecular weight of about 400 to 5,000 and comprises an EO—PO—EO block copolymer and/or a $C_{10}$-$C_{18}$ alcohol-EO—PO block copolymer; and (c) the co-hardening agent may include mineral oil, naphthenic oil, isopropyl myristate, one or more $C_{12}$-$C_{16}$ aliphatic alcohols and/or one or more ethoxylated $C_{12}$-$C_{16}$ aliphatic alcohols with no more than about 1 mole average degree of ethoxylation; and the co-hardening agent may have a solubility in water of less than about 0.1 wt. %; and may have a flash point of at least about 90° C. In some embodiments, the composition may be a gel having a hardness of at least about 250 g and a gel melt temperature of about 60-70° C.

In some embodiments, the composition may further include one or more of: (e) polyol humectant; (f) a fragrance component; (g) a nonionic surfactant which is different from the ethoxylated alcohol or the ethylene oxide-propylene oxide block copolymer; (h) a natural gum or synthetic polymer resin; (i) anionic, cationic, zwitterionic and/or amphoteric surfactant; and (j) one or more cleaning adjuvant materials selected from the group consisting of antimicrobial agent(s), water-soluble dye(s), pigment(s), complexing agent(s), surface modifying polymer(s), preservative agent(s), enzyme(s), bleach(es), pH adjusting agent(s), anti-scale forming agent(s), abrasive(s), dispersant(s), and solvent(s).

In some embodiments, the composition may include: (a) about 20 to 30 wt. % of the ethoxylated alcohol; (b) about 3 to 10 wt. % of the ethylene oxide-propylene oxide block copolymer; and (c) about 1.5 to 4 wt. % of the co-hardening agent. In some embodiments, the composition may further include about 1-10 wt. % of a fragrance component; and about 1-10 wt. % polyol humectant. In some embodiments, the ethylene oxide-propylene oxide block copolymer may include $C_{12}$-$C_{15}$ alcohol EO—PO adduct and/or an EO—PO—EO block copolymer. The EO—PO—EO block copolymer may include about 30 to 50 wt. % EO units and may have an average molecular weight of about 1,000 to 5,000. The $C_{12}$-$C_{15}$ alcohol EO—PO adduct may have an average molecular weight of about 500 to 2,000.

In one aspect, the cleaning composition may include: (a) about 15 to 40 wt. % of an ethoxylated $C_{16}$-$C_{30}$ aliphatic alcohol that may have an average of 20 to 50 ethylene oxide units; (b) about 1 to 10 wt. % ethylene oxide-propylene oxide block copolymer; (c) about 1.5 to 5 wt. % of a hydrocarbon or oxygenated hydrocarbon co-hardening agent; and (d) at least about 25 wt. % water. In some embodiments, the composition may be a gel having a hardness at 22° C. of at least about 150 g and a gel melt temperature of about 50 to 90° C. In some embodiments, the composition may include: (a) about 20 to 35 wt. % of the ethoxylated alcohol; (b) about 3 to 8 wt. % of the ethylene oxide-propylene oxide block copolymer; (c) about 1 to 5 wt. % of the co-hardening agent; and (d) at least about 40 wt. % water; wherein the gel may have a hardness at 22° C. of at least about 200 g and a gel melt temperature of about 55 to 70° C. The composition may further include (e) about 2-10 wt. % of a second ethoxylated alcohol, which may be an ethoxylated $C_8$-$C_{15}$ aliphatic alcohol having an average of 5 to 15 ethylene oxide units; and/or (f) about 2-10 wt. % polyol humectant. In some embodiments, the co-hardening agent may include mineral oil, naphthenic oil, paraffin oil, an alkyl ester of a $C_{10}$-$C_{22}$ fatty acid, a $C_{10}$-$C_{22}$ aliphatic alcohol and/or a $C_{10}$-$C_{22}$ aliphatic alcohol ethoxylate with no more than about 1 mole average degree of ethoxylation; and the co-hardening agent may have a solubility in water of less than about 0.1 wt. %; and may have a flash point of at least about 90° C.

In some embodiments, the composition may consists of: (a) about 20 to 30 wt. % of the ethoxylated alcohol, which may be an ethoxylated $C_{16}$-$C_{22}$ linear aliphatic alcohol having an average of 20 to 30 ethylene oxide units; (b) about 3 to 10 wt. % of the ethylene oxide-propylene oxide block copolymer; (c) about 1.5 to 3 wt. % mineral oil; (d) at least about 40 wt. % water; (e) 0 to about 1 wt. % of a natural gum and/or synthetic polymer resin; (f) 0 to about 10 wt. % of a fragrance component; (g) 0 to about 10 wt. % of a polyol humectant; (h) 0 to about 10 wt. % of a nonionic surfactant which is different from the ethoxylated $C_{16}$-$C_{22}$ linear aliphatic alcohol; and (i) 0 to about 10 wt. % of one or more cleaning adjuvant materials.

In some embodiments, the composition may include (a) about 15-40 wt. % of the ethoxylated alcohol, which includes an ethoxylated $C_{16}$-$C_{30}$ alcohol having an average of 20 to 50 ethylene oxide units; (b) about 1-15 wt. % of the ethylene oxide-propylene oxide block copolymer; (c) about 0.5-10 wt. % mineral oil; and (d) at least about 25 wt. % water. In some embodiments, the composition may further include (e) about 1-10 wt. % of a fragrance component and/or (f) about 1-10 wt. % glycerin.

In some embodiments, the composition may include (a) about 15-40 wt. % of the ethoxylated alcohol, which may include an ethoxylated $C_{16}$-$C_{22}$ alcohol having an average of 20 to 50 ethylene oxide units; (b) about 1-15 wt. % of the ethylene oxide-propylene oxide block copolymer; (c) about 0.5-10 wt. % mineral oil; and (d) at least about 25 wt. % water. In certain embodiments, the composition may further include (e) about 1-10 wt. % of a fragrance component; and optionally (f) about 1-10 wt. % glycerin. The ethoxylated alcohol may include an ethoxylated $C_{16}$-$C_{30}$ aliphatic alcohol having an average of about 20 to 50 ethylene oxide units and an ethoxylated $C_8$-$C_{15}$ aliphatic alcohol having an average of about 5 to 15 ethylene oxide units. In some embodiments, the composition may further include one or more of: (e) polyol humectant; (f) a fragrance component; (g) a nonionic surfactant which is different from the first ethoxylated alcohol; (h) a natural or synthetic polymer resin; (i) anionic, cationic, zwitterionic and/or amphoteric surfactant; and (j) one or more adjuvants. In some embodiments, the composition may further include an nonionic surfactant which is different from the first ethoxylated alcohol. In certain aspects, the composition may be self-adhering upon application to a hard surface.

In another aspect, the cleaning composition may include (a) a first ethoxylated alcohol, which may be an ethoxylated $C_{16}$-$C_{30}$ alcohol having an average of 20 to 50 ethylene oxide units; (b) ethylene oxide-propylene oxide block copolymer; (c) mineral oil; and (d) water. In some embodiments, the composition may be self-adhering upon application to a hard surface. The composition may further include one or more of: (e) polyol humectant; (f) a fragrance component; (g) a nonionic surfactant which is different from the first ethoxylated alcohol; (h) a natural or synthetic polymer resin; (i) anionic, cationic, zwitterionic and/or amphoteric surfactant; and (j) one or more adjuvants. In some embodiments, the composition may include (a) about 15-35 wt. % of the first ethoxylated alcohol; (b) about 1-15 wt. % of the ethylene oxide-propylene oxide block copolymer; and (c) about 0.5-10 wt. % of the mineral oil. The composition may further include about 1-10 wt. % of a fragrance component; and about 1-10 wt. % polyol humectant. In some embodiments, the ethylene oxide-propylene oxide block copolymer may include an EO—PO block copolymer, an EO—PO—EO block copolymer, a $C_8$-$C_{18}$ alcohol EO—PO adduct, a $C_8$-$C_{18}$ alcohol PO—EO adduct, and/or an EO—PO dialkyl ether. In some embodiments, the composition may include (a) about 20-30 wt. % of the first ethoxylated alcohol; (b) about 2-10 wt. % of the ethylene oxide-propylene oxide block copolymer; (c) about 0.5-5 wt. % of the mineral oil; (d) at least about 25 wt. % water; (e) about 2-10 wt. % glycerin; (f) about 1-10 wt. % of a fragrance component; and (g) about 0-10 wt. % of a second ethoxylated alcohol, which may be an ethoxylated $C_8$-$C_{15}$ alcohol having an average of 5 to 12 ethylene oxide units. The composition may be a gel having a hardness of at least about 150 g and a gel melt temperature of about 50-90° C.

In one aspect, an cleaning composition may include (a) about 15-40 wt. % of a first ethoxylated alcohol, which may be an ethoxylated $C_{14}$-$C_{30}$ alcohol having an average of about 20 to 50 ethylene oxide units; (b) about 1-15 wt. % ethylene oxide-propylene oxide block copolymer; (c) about 0.5-10 wt. % mineral oil; and (d) water. In some embodiments, the composition may include (a) about 20-35 wt. % of the first ethoxylated alcohol, which may include an ethoxylated $C_{14}$-$C_{22}$ alcohol having an average of 20 to 40 ethylene oxide units; (b) about 2-10 wt. % of the ethylene oxide-propylene oxide block copolymer; (c) about 0.5-5 wt. % of the mineral oil; (d) at least about 25 wt. % water; and further include (e) about 1-10 wt. % of a second ethoxylated alcohol, which may be an ethoxylated $C_8$-$C_{15}$ alcohol having an average of 5 to 15 ethylene oxide units; and (f) about 2-10 wt. % polyol humectant. In certain embodiments, the composition may consist of: (a) about 15-40 wt. % of the first ethoxylated alcohol, which may be an ethoxylated $C_{14}$-$C_{22}$ alcohol having an average of 15 to 50 ethylene oxide units; (b) about 1-10 wt. % of the ethylene oxide-propylene oxide block copolymer; (c) about 0.5-10 wt. % mineral oil; (d) at least about 40 wt. % water; (e) 0 to about 3 wt. % of a natural or synthetic polymer resin; (f) 0 to about 10 wt. % of a fragrance component; (g) 0 to about 15 wt. % of a polyol humectant; (h) 0 to about 10 wt. % of a nonionic surfactant which is different from the first ethoxylated alcohol; and (i) 0 to about 10 wt. % of one or more adjuvants. The composition may include an anionic, cationic, zwitterionic, and/or amphoteric surfactant. In some embodiments, the first ethoxylated alcohol may include an ethoxylated linear $C_{16}$-$C_{22}$ primary alcohol having an average of 20-35 ethylene oxide units. The composition may further include a nonionic surfactant which is different from the first ethoxylated alcohol. In some embodiments, the composition may be a gel that has a hardness of at least about 150 g and a gel melt temperature of about 50-80° C. The composition may be self-adhering upon application to a hard surface.

In another aspect, a cleaning composition may include an ethoxylated alcohol, an poly(ethylene oxide-propylene oxide) block copolymer, mineral oil, and water. The composition may have a hardness value of at least about 150 grams. In some embodiments, the composition may be a gel. The ethoxylated alcohol may include a terminal alkyl group with at least 12 carbon atoms. In some embodiments, the ethoxylated alcohol may include a terminal $C_{16}$-$C_{30}$ alkyl group or a terminal $C_{16}$-$C_{22}$ alkyl group. The ethoxylated alcohol may include at least about 15 ethylene oxide units. In some embodiments, the ethoxylated alcohol may include about 20-50 ethylene oxide units or about 20-35 ethylene oxide units. The composition may further include a second ethoxylated alcohol that is different from the first ethoxylated alcohol. The second ethoxylated alcohol may include a terminal $C_8$-$C_{15}$ alkyl group having 5-15 ethylene oxide units. The ethylene oxide-propylene oxide block copolymer may have a molecular weight of about 400 to about 10,000. The composition may be substantially free of cationic surfactants. The composition may be substantially free of anionic surfactants. The composition may have a gel melt temperature from about 50 to 90° C. In some embodiments, the composition may have a gel melt temperature from about 55-75° C. In some embodiments, the composition may have a gel melt temperature from about 60-70° C. The composition may further include one or more of a polyol, natural gum, synthetic polymer resin, dye, surface-modifying polymer, antimicrobial agent, or other cleaning agent auxiliary ingredients. In some embodiments, the polyol may include glycerin and/or sorbitol. The composition may include about 15-40 wt. % of the ethoxylated alcohol, about 1-10 wt. % of the ethylene oxide-propylene oxide block copolymer, about 0.5-10 wt. % of the mineral oil, and at least about 25 wt. % water. In some embodiments, the composition may include at least about 40 wt. % water. In some embodiments, the composition may self-adhere to a hard surface. The hard surface may be an inclined or vertical surface. In some embodiments, the hard surface may be part of an interior bowl of a toilet.

In one aspect, a cleaning composition may consist essential of an ethoxylated alcohol, an ethylene oxide-propylene oxide block copolymer, a mineral oil, water, optionally a second ethoxylated alcohol, and optionally one or more of an anionic surfactant, polyol, natural gum, synthetic polymer resin, dye, surface-modifying polymer, antimicrobial agent, or other cleaning agent auxiliary ingredients. In some embodiments, the composition may consist essentially of about 15-40 wt. % of the ethoxylated alcohol, about 1-10 wt. % of the polyethylene oxide-polypropylene oxide block copolymer, about 0.5-10 wt. % of the mineral oil, about 0-10 wt. % of a second ethoxylated alcohol that is different from the first ethoxylated alcohol, about 0-10 wt. % of a nonionic surfactant that is different from the first and second ethoxylated alcohols, about 0-10 wt. % of one or more fragrances, about 0-10 wt. % of a polyol, and at least about 40 wt. % water. The composition may consist essentially of about 20-30 wt. % of the ethoxylated alcohol, about 4-8 wt. % of the poly(ethylene oxide-propylene oxide) block copolymer, about 1-3 wt. % of the mineral oil, about 1-10 wt. % of a second ethoxylated alcohol that is different from the first ethoxylated alcohol, about 0-6 wt. % of a nonionic surfactant that is different from the first and second ethoxylated alcohols, about 1-5 wt. % of one or more fragrances, about 1-5 wt. % of glycerin, and at least about 40 wt. % water. In some embodiments, the ethoxylated alcohol may include a $C_{16}$-$C_{22}$ terminal alkyl group and an average of about 20-30 ethylene oxide units. The second ethoxylated alcohol may include a $C_{10}$-$C_{15}$ terminal alkyl group and 6-12 ethylene oxide units.

In another aspect, the composition may be an adhesive cleaning composition that is self-adhering upon application to a hard surface and may include (a) a first ethoxylated alcohol, which is an ethoxylated $C_{12}$-$C_{30}$ alcohol having an average of 15 to 50 ethylene oxide units; (b) ethylene oxide-propylene oxide block copolymer; (c) mineral oil; and (d) water. In some embodiments, the composition may further include one or more of (e) polyol humectant; (f) a fragrance component; (g) a nonionic surfactant which is different from the first ethoxylated alcohol; (h) a natural or synthetic polymer resin; (i) anionic, cationic, zwitterionic and/or amphoteric surfactant; and (j) one or more adjuvants.

In some embodiments, the composition may include a) about 15-35 wt. % of the first ethoxylated alcohol; (b) about 1-15 wt. % of the ethylene oxide-propylene oxide block copolymer; and (c) about 0.5-10 wt. % of the co-hardening agent, such as mineral oil. The composition may further include about 1-10 wt. % of a fragrance component; and optionally, about 1-10 wt. % polyol humectant. In another embodiment, the composition may include (a) about 20-30 wt. % of the first ethoxylated alcohol; (b) about 2-10 wt. % of the ethylene oxide-propylene oxide block copolymer; (c) about 0.5-5 wt. % of the mineral oil or other co-hardening agent; (d) at least about 25 wt. % water; (e) about 2-10 wt. % glycerin; (f) about 1-10 wt. % of a fragrance component; and (g) about 0-10 wt. % of a second ethoxylated alcohol, which is an ethoxylated $C_8$-$C_{15}$ alcohol having an average of 5 to 15 ethylene oxide units. In some embodiments, the ethylene oxide-propylene oxide block copolymer may include an EO—PO block copolymer, an EO—PO—EO block copolymer, a $C_8$-$C_{18}$ alcohol EO—PO adduct, a $C_8$-$C_{18}$ alcohol PO—EO adduct and/or an EO—PO dialkyl ether. In some embodiments, the cleaning composition may be a gel and have a gel hardness of at least about 150 g, and/or a gel melt temperature of about 50-90° C.

In another aspect, the composition may be a gel cleaning composition that includes (a) about 15-40 wt. % of a first ethoxylated alcohol, which is an ethoxylated $C_{14}$-$C_{30}$ alcohol having an average of 15 to 50 ethylene oxide units; (b) about 1-15 wt. % ethylene oxide-propylene oxide block copolymer; (c) about 0.5-10 wt. % mineral oil; and (d) water. In some embodiments, the composition may include (a) about 20-35 wt. % of the first ethoxylated alcohol, which may include an ethoxylated $C_{14}$-$C_{22}$ alcohol having an average of 20 to 40 ethylene oxide units; (b) about 2-10 wt. % of the ethylene oxide-propylene oxide block copolymer; (c) about 0.5-5 wt. % of the mineral oil; (d) at least about 25 wt. % water. The composition may further include (e) about 1-10 wt. % of a second ethoxylated alcohol, which is an ethoxylated $C_8$-$C_{15}$ alcohol having an average of 5 to 15 ethylene oxide units and (f) about 2-10 wt. % polyol humectant. In some embodiments, the composition may also include an anionic, cationic, zwitterionic and/or amphoteric surfactant. In another embodiment, the composition may also include a nonionic surfactant which is different from the first ethoxylated alcohol. In some embodiments, the first ethoxylated alcohol may include an ethoxylated linear $C_{14}$-$C_{22}$ primary alcohol having an average of 20-35 ethylene oxide units. In some embodiments, the cleaning composition may be a gel and have a gel hardness of at least about 150 g and/or a gel melt temperature of about 50-90° C. The composition may be self-adhering upon application to a hard surface.

In another aspect, the composition may be an adhesive cleaning composition that is self-adhering upon application to a hard surface and may include (a) polyalkoxy nonionic surfactant; (b) co-hardening agent, which includes an alkyl ester of a $C_{10}$-$C_{22}$ aliphatic carboxylic acid; and (c) at least about 25 wt. % and, typically, at least about 40 wt. % water. In some embodiments, the polyalkoxy nonionic surfactant may include ethoxylated $C_{12}$-$C_{30}$ aliphatic alcohol having an average of 15 to 50 ethylene oxide units and/or alkylene oxide block copolymer having. For example, polyalkoxy nonionic surfactant may include an ethoxylated C12-C22 fatty alcohol having an average of about 15 to 50 ethylene oxide units (often having an average of about 20 to 40 ethylene oxide units) and/or ethylene oxide-propylene oxide block copolymer having an average of at least about 15 alkylene oxide units. The adhesive cleaning composition may further include one or more of (e) polyol humectant; (f) a fragrance component; (g) a nonionic surfactant which is different from the first ethoxylated alcohol; (h) a natural or synthetic polymer resin; (i) anionic, cationic, zwitterionic and/or amphoteric surfactant; and (j) one or more adjuvants. The co-hardening agent commonly has a water solubility of no more than about 0.1 wt. % and/or a flash point of at least about 90° C.

In another aspect, the composition may be a gel cleaning composition that includes (a) about 15-40 wt. % ethoxylated alcohol, e.g., an ethoxylated $C_{14}$-$C_{30}$ aliphatic alcohol having an average of 15 to 50 ethylene oxide units; (b) optionally, about 1-15 wt. % ethylene oxide-propylene oxide block copolymer; (c) about 0.5-10 wt. % co-hardening agent, which includes an alkyl ester of a $C_{10}$-$C_{22}$ aliphatic carboxylic acid; and (d) water. In some embodiments, the composition may include (a) about 20-35 wt. % of the ethoxylated $C_{14}$-$C_{30}$ aliphatic alcohol, which may include an ethoxylated $C_{14}$-$C_{22}$ fatty alcohol having an average of about 20 to 40 ethylene oxide units; (b) optionally, about 2-10 wt. % of the ethylene oxide-propylene oxide block copolymer; (c) about 0.5-5 wt. % of the co-hardening agent; (d) at least about 25 wt. % water. The composition may further include about 2-10 wt. % polyol humectant, e.g., glycerin. In some embodiments, the composition may also include an anionic, cationic, zwitterionic and/or amphoteric surfactant. In some embodiments, the composition may also include a different nonionic surfactant. Typically, the cleaning composition is a gel having a gel melt temperature of about 50-90° C. The gel may have a gel hardness of at least about 150 g.

In another aspect, the present cleaning composition may include (a) about 15 to 40 wt. % of a polyalkoxy nonionic surfactant; (b) about 1 to 10 wt. % co-hardening agent, which includes an alkyl ester of a $C_{10}$-$C_{22}$ aliphatic carboxylic acid; and (c) at least about 25 wt. % water. Such a cleaning composition may be a self-adhesive gel having a melt temperature of at least about 50° C. In some instances, such a cleaning composition may include a polyalkoxy nonionic surfactant which has an average of at least about 15 alkylene oxide units. For example, the polyalkoxy nonionic surfactant may be an ethoxylated linear aliphatic alcohol and/or polymeric alkylene oxide block copolymer. In some instances, the ethoxylated linear aliphatic alcohol may include an ethoxylated $C_{14}$-$C_{30}$ linear aliphatic alcohol having an average of about 15 to 50 ethylene oxide units and commonly, an ethoxylated $C_{14}$-$C_{22}$ fatty alcohol having an average of about 20 to 40 ethylene oxide units. The polymeric alkylene oxide block copolymer may be an ethyleneoxide-propyleneoxide block copolymer. Typically, the co-hardening agent has a water solubility of no more than about 0.1 wt. % and/or a flash point of at least about 90° C. Examples of suitable $C_{10}$-$C_{22}$ aliphatic carboxylic acid alkyl esters which may be used as the co-hardening agent include isopropyl myristate, ethyl palmitate, isopropyl palmitate, n-butyl myristate, n-hexyl laurate, ethyl stearate, isopropyl stearate, n-butyl laurate and/or ethyl oleate. The co-hardening agent may also include mineral oil, naphthenic oil, paraffin oil, a $C_{12}$-$C_{18}$ aliphatic alcohol, and/or a $C_{10}$-$C_{18}$ aliphatic alcohol ethoxylate with an average degree of ethoxylation of no more than about 2.

Illustrative examples of the cleaning composition described in the preceding paragraph includes cleaning gels which include about 20-30 wt. % of ethoxylated $C_{14}$-$C_{22}$ fatty alcohol having an average about 15 to 50 ethylene oxide units; about 0.5-5 wt. % of the co-hardening agent; and at least about 40 wt. % water. Such as cleaning gel may also include about 2-10 wt. % glycerin; about 0-10 wt. % of a fragrance component; and about 0-10 wt. % of an ethoxylated $C_8$-$C_{15}$ aliphatic alcohol having an average of 5 to 12 ethylene oxide units. Such compositions may also include a polymeric alkylene oxide block copolymer, such as an ethyleneoxide-propyleneoxide block copolymer. The co-hardening agent may suitably include a $C_1$-$C_6$ alkyl ester of a $C_{10}$-$C_{18}$ aliphatic carboxylic acid; e.g., a $C_2$-$C_6$ alkyl ester of a $C_{12}$-$C_{16}$ fatty acid. In many instances, the cleaning compositions described in this and the preceding paragraph the polyalkoxy nonionic surfactant may include an ethoxylated $C_{14}$-$C_{30}$ aliphatic alcohol having an average of about 20 to 50 ethylene oxide units and/or ethylene oxide-propylene oxide block copolymer having a molecular weight of about 1,000 to 5,000. Such compositions may also include fragrance, colorant, polyol humectant, preservative, antimicrobial agent, solvent, bleaching agent, abrasive, anti-scale agent, and/or pH adjusting agent. In some instances, such compositions may also include a cationic surfactant.

The cleaning composition described in the paragraph above may also include about 1-10 wt. % of a fragrance component and/or about 1 to 10 wt. % ethylene oxide-propylene oxide block copolymer. In some instances, the cleaning compositions described in this paragraph may also include a polysaccharide and/or synthetic polymer resin. In some instances, the cleaning compositions described in this paragraph may also include a cationic surfactant. In some instances, the cleaning compositions described in this paragraph may also include one or more components selected from (e) polyol humectant; (f) a fragrance component; (g) a nonionic surfactant which is different from the ethoxylated alcohol or the ethylene oxide-propylene oxide block copolymer; (h) a natural gum or synthetic polymer resin; (i) anionic, cationic, zwitterionic and/or amphoteric surfactant; and (j) one or more cleaning adjuvant materials selected from the group consisting of antimicrobial agent(s), water-soluble dye(s), pigment(s), complexing agent(s), surface modifying polymer(s), preservative agent(s), enzyme(s), bleach(es), pH adjusting agent(s), anti-scale forming agent(s), abrasive(s), dispersant(s), and solvent(s).

In another aspect, the present cleaning composition may include (a) ethoxylated $C_{14}$-$C_{30}$ alcohol having an average of about 20 to 50 ethoxy units; (b) polyol humectant; (c) co-hardening agent, which includes an alkyl ester of a $C_{10}$-$C_{22}$ aliphatic acid; and (d) at least about 25 wt. % water. Such cleaning compositions may be a gel having a melt temperature of at least about 50° C. and often a gel melt temperature of about 50 to 90° C. In such compositions, the co-hardening agent may also include mineral oil, naphthenic oil, paraffin oil, $C_{10}$-$C_{22}$ alcohol and/or $C_{10}$-$C_{22}$ alcohol ethoxylate with no more than about 2 mole average degree of ethoxylation. The co-hardening agent desirably has a solubility in water of no more than about 0.1 wt. % and/or a flash point of at least about 90° C. For example, cleaning composition may be a gel which includes (a) about 15 to 35 wt. % of ethoxylated $C_{14}$-$C_{30}$ fatty alcohol; (b) about 1-10 wt. % of the polyol humectant; (c) about 0.5 to 5 wt. % of the co-hardening agent; and (d) at least about 40 wt. % water. This cleaning composition may also include about 1-10 wt. % of a fragrance component and/or about 1 to 10 wt. % ethylene oxide-propylene oxide block copolymer. In some instances, the cleaning compositions described in this paragraph may also include a polysaccharide and/or synthetic polymer resin. In some instances, the cleaning compositions described in this paragraph may also include a cationic surfactant. In some instances, the cleaning compositions described in this paragraph may also include one or more components selected from (e) polyol humectant; (f) a fragrance component; (g) a nonionic surfactant which is different from the ethoxylated alcohol or the ethylene oxide-propylene oxide block copolymer; (h) a natural gum or synthetic polymer resin; (i) anionic, cationic, zwitterionic and/or amphoteric surfactant; and (j) one or more cleaning adjuvant materials selected from the group consisting of antimicrobial agent(s), water-soluble dye(s), pigment(s), complexing agent(s), surface modifying polymer(s), preservative agent(s), enzyme(s), bleach(es), pH adjusting agent(s), anti-scale forming agent(s), abrasive(s), dispersant(s), and solvent(s).

While certain embodiments have been illustrated and described, it should be understood that changes and modifications can be made therein in accordance with ordinary skill in the art without departing from the technology in its broader aspects.

The embodiments, illustratively described herein may suitably be practiced in the absence of any element or elements, limitation or limitations, not specifically disclosed herein. Thus, for example, the terms "comprising," "including," "containing," shall be read expansively and without limitation. Additionally, the terms and expressions employed herein have been used as terms of description and not of limitation, and there is no intention in the use of such terms and expressions of excluding any equivalents of the features shown and described or portions thereof, but it is recognized that various modifications are possible within the scope of the claimed technology. Additionally, the phrase "consisting essentially of" will be understood to include those elements specifically recited and those additional elements that do not materially affect the basic and novel characteristics of the claimed technology. The phrase "consisting of" excludes any element not specified.

As used herein, "about" will be understood by persons of ordinary skill in the art and will vary to some extent depending upon the context in which it is used. If there are uses of the term which are not clear to persons of ordinary skill in the art, given the context in which it is used, "about" will mean up to plus or minus 10% of the particular term.

The use of the terms "a" and "an" and "the" and similar referents in the context of describing the elements (especially in the context of the following claims) are to be construed to cover both the singular and the plural, unless otherwise indicated herein or clearly contradicted by context. Recitation of ranges of values herein are merely intended to serve as a shorthand method of referring individually to each separate value falling within the range, unless otherwise indicated herein, and each separate value is incorporated into the specification as if it were individually recited herein. All methods described herein can be performed in any suitable order unless otherwise indicated herein or otherwise clearly contradicted by context. The use of any and all examples, or exemplary language (e.g., "such as") provided herein, is intended merely to better illuminate the embodiments and does not pose a limitation on the scope of the claims unless otherwise stated. No language in the specification should be construed as indicating any non-claimed element as essential.

In addition, where features or aspects of the disclosure are described in terms of Markush groups, those skilled in the art will recognize that the disclosure is also thereby described in terms of any individual member or subgroup of members of the Markush group.

As will be understood by one skilled in the art, for any and all purposes, particularly in terms of providing a written description, all ranges disclosed herein also encompass any and all possible subranges and combinations of subranges thereof.

What is claimed is:

1. A cleaning composition comprising:
   (a) about 15 to 40 wt. % of an ethoxylated alcohol having an average of about 20 to 50 ethoxy units;
   (b) about 3 to 15 wt. % of a polymeric alkylene oxide block copolymer;
   (c) about 1.5 to 10 wt. % of an oxygenated hydrocarbon co-hardening agent, which comprises an alkyl ester of a $C_{10}$-$C_{22}$ fatty acid, a $C_{10}$-$C_{22}$ aliphatic alcohol and/or a $C_{10}$-$C_{22}$ aliphatic alcohol ethoxylate with no more than about 1 mole average degree of ethoxylation; and
   (d) at least about 25 wt. % water;
   wherein the composition is a self-adhesive gel having a hardness at 22° C. of at least about 200 g and a gel melt temperature of about 50 to 90° C.; and the oxygenated hydrocarbon co-hardening agent has a solubility in water of less than about 0.1 wt. %.

2. The composition of claim 1, wherein the ethoxylated alcohol comprises ethoxylated $C_{16}$-$C_{30}$ linear aliphatic alcohol; and the polymeric alkylene oxide block copolymer comprises an ethylene oxide-propylene oxide block copolymer.

3. The composition of claim 1, wherein the ethoxylated alcohol is an ethoxylated $C_{16}$-$C_{30}$ linear aliphatic alcohol; the polymeric alkylene oxide block copolymer is an ethylene oxide-propylene oxide block copolymer; and
   (c) the oxygenated hydrocarbon co-hardening agent comprises the fatty acid alkyl ester.

4. The composition of claim 2, wherein the ethylene oxide-propylene oxide block copolymer comprises an EO-PO-EO block copolymer and/or a $C_{10}$-$C_{18}$ aliphatic alcohol-EO-PO block copolymer and/or a $C_{10}$-$C_{18}$ aliphatic alcohol-PO-EO block copolymer.

5. The composition of claim 2, wherein the ethylene oxide-propylene oxide block copolymer has an average molecular weight of about 600 to 5,000.

6. The composition of claim 1, wherein the composition further comprises mineral oil, naphthenic oil, and/or paraffin oil.

7. The composition of claim 1, wherein the oxygenated hydrocarbon co-hardening agent has a flash point of at least about 90° C.

8. The composition of claim 1 further comprising one or more of:
   (e) polyol humectant;
   (f) a fragrance component;
   (g) a nonionic surfactant, which is different from the ethoxylated alcohol or the ethylene oxide-propylene oxide block copolymer;
   (h) a natural gum or synthetic polymer resin;
   (i) anionic, cationic, zwitterionic and/or amphoteric surfactant; and
   (j) one or more cleaning adjuvant materials selected from the group consisting of antimicrobial agent(s), water-soluble dye(s), pigment(s), complexing agent(s), surface modifying polymer(s), preservative agent(s), enzyme(s), bleach(es), pH adjusting agent(s), anti-scale forming agent(s), abrasive(s), dispersant(s), and solvent(s).

9. The composition of claim 1, wherein the ethoxylated alcohol comprises an ethoxylated $C_{16}$-$C_{22}$ linear aliphatic alcohol having an average of about 20 to 40 ethylene oxide units.

10. The composition of claim 1, wherein the composition is a gel having a hardness of at least about 225 g and a gel melt temperature of about 55-75° C.

11. The composition of claim 1 wherein the composition is self-adhering upon application to a hard surface.

12. The composition of claim 1, wherein (a) the ethoxylated alcohol comprises an ethoxylated $C_{16}$-$C_{22}$ fatty alcohol having an average of about 20 to 40 ethylene oxide units;
   (b) the polymeric alkylene oxide block copolymer has an average molecular weight of about 600 to 5,000 and comprises an EO-PO-EO block copolymer, a $C_{10}$-$C_{18}$ aliphatic alcohol-EO-PO block copolymer and/or a $C_{10}$-$C_{18}$ aliphatic alcohol-PO-EO block copolymer; and
   (c) the oxygenated hydrocarbon co-hardening agent has a flash point of at least about 90° C., and comprises one or more $C_1$-$C_6$ alkyl esters of a $C_{10}$-$C_{22}$ fatty acid.

13. The composition of claim 12, wherein the ethoxylated $C_{16}$-$C_{22}$ linear aliphatic alcohol is a peaked ethoxylated $C_{16}$-$C_{22}$ linear aliphatic alcohol.

14. The composition of claim 1, wherein the composition includes no more than about 0.5 wt. % polyethylene glycol.

15. The composition of claim 1, further comprising a cationic surfactant.

16. A cleaning composition comprising:
   (a) about 15 to 40 wt. % of an ethoxylated $C_{14}$-$C_{30}$ linear aliphatic alcohol having an average of about 20 to 50 ethylene oxide units;
   (b) about 3 to 10 wt. % ethylene oxide-propylene oxide block copolymer;
   (c) about 1.5 to 5 wt. % of a co-hardening agent comprising an alkyl ester of a $C_{10}$-$C_{22}$ fatty acid, a $C_{10}$-$C_{22}$ aliphatic alcohol and/or a $C_{10}$-$C_{22}$ aliphatic alcohol ethoxylate with no more than about 1 mole average degree of ethoxylation;
   (d) at least about 40 wt. % water; and
   (e) about 2 to 6 wt. % of an ethoxylated $C_8$-$C_{15}$ alcohol having an average of 5 to 15 ethylene oxide units;
   wherein the composition is a self-adhesive gel having a hardness at 22° C. of at least about 200 g and a gel melt temperature of about 50 to 90° C.; and the co-hardening agent has a solubility in water of less than about 0.1 wt. %.

17. The composition of claim 16, wherein the co-hardening agent comprises one or more $C_1$-$C_6$ alkyl esters of a $C_{10}$-$C_{22}$ fatty acid and has a flash point of at least about 90° C.

18. The composition of claim 17, wherein the cleaning gel comprises:
(a) about 15 to 30 wt. % of an ethoxylated $C_{14}$-$C_{22}$ fatty alcohol having an average of about 20 to 40 ethylene oxide units;
(c) about 1.5 to 3 wt. % of the co-hardening agent;
and further comprises:
(f) about 1 to 10 wt. % polyol humectant; and
(e) about 1 to 10 wt. % fragrance.

19. The composition of claim 18, wherein the gel has a hardness at 22° C. of at least about 225 g and a gel melt temperature of about 55 to 75° C.

20. A cleaning composition comprising:
(a) about 15 to 40 wt. % of a polyalkoxy nonionic surfactant, which comprises ethylene oxide-propylene oxide block copolymer and ethoxylated $C_{14}$-$C_{30}$ aliphatic alcohol having an average of about 15 to 50 ethylene oxide units;
(b) about 1.5 to 10 wt. % co-hardening agent, which includes an alkyl ester of a $C_{10}$-$C_{22}$ aliphatic carboxylic acid, wherein the co-hardening agent has a water solubility of no more than about 0.1 wt. % and a flash point of at least about 90° C.; and
(c) at least about 25 wt. % water; and
(d) optionally about 2 to 6 wt. % of an ethoxylated $C_8$-$C_{15}$ alcohol having an average of 5 to 15 ethylene oxide units;
wherein the composition is a self-adhesive gel having a melt temperature of about 50 to 90° C. and a hardness at 22° C. of at least about 200 g.

21. The composition of claim 20, wherein the polyalkoxy nonionic surfactant has an average of at least about 15 alkylene oxide units.

22. The composition of claim 21, wherein the ethoxylated $C_{14}$-$C_{30}$ aliphatic alcohol is an ethoxylated $C_{14}$-$C_{22}$ fatty alcohol.

23. The composition of claim 20, wherein the co-hardening agent further comprises mineral oil, naphthenic oil, paraffin oil, a $C_{12}$-$C_{18}$ aliphatic alcohol, and/or a $C_{10}$-$C_{18}$ aliphatic alcohol ethoxylate with an average degree of ethoxylation of no more than about 1.

24. The composition of claim 20, wherein the alkyl ester of the $C_{10}$-$C_{22}$ aliphatic carboxylic acid comprises isopropyl myristate, ethyl palmitate, isopropyl palmitate, n-butyl myristate, n-hexyl laurate, ethyl stearate, isopropyl stearate, n-butyl laurate and/or ethyl oleate.

25. The composition of claim 20, further comprising:
(e) about 2 to 10 wt. % polyol humectant; and
(f) about 1 to 10 wt. % of a fragrance component.

26. The composition of claim 20, wherein the alkyl ester co-hardening agent comprises a $C_2$-$C_6$ alkyl ester of a $C_{10}$-$C_{18}$ fatty acid.

27. The composition of claim 20, further comprising a cationic surfactant.

28. The composition of claim 20, comprising:
(a) about 15 to 30 wt. % ethoxylated C14-C22 fatty alcohol having an average of about 15 to 40 ethylene oxide units;
(b) about 0.5 to 5 wt. % of the co-hardening agent;
(c) at least about 40 wt. % water; and
(d) about 1-10 wt. % polyol humectant.

29. The composition of claim 20, further comprising about 2 to 6 wt. % of an ethoxylated $C_8$-$C_{15}$ alcohol having an average of 5 to 12 ethylene oxide units.

30. The composition of claim 20, wherein the composition contains less than about 0.1 wt. % anionic surfactant.

31. The composition of claim 16, wherein the composition contains less than about 0.1 wt. % anionic surfactant.

* * * * *